United States Patent
Namer et al.

(10) Patent No.: US 12,409,242 B2
(45) Date of Patent: Sep. 9, 2025

(54) FAR-UVC, NARROW-BAND OF DISINFECTING LIGHT, USED IN AIRCRAFT CABIN

(71) Applicant: Zodiac Cabin Controls GmbH, Hamburg (DE)

(72) Inventors: Arnaud Jacques Namer, Torrance, CA (US); Volker Antonczyk, Hamburg (DE); Michael Glück, Hamburg (DE); Michael Paul, Hamburg (DE)

(73) Assignee: Zodiac Cabin Controls GmbH, Hamburg (DE)

( * ) Notice: Subject to any disclaimer, the term of this patent is extended or adjusted under 35 U.S.C. 154(b) by 317 days.

(21) Appl. No.: 17/913,804

(22) PCT Filed: Mar. 30, 2021

(86) PCT No.: PCT/IB2021/052667
§ 371 (c)(1),
(2) Date: Sep. 22, 2022

(87) PCT Pub. No.: WO2021/214574
PCT Pub. Date: Oct. 28, 2021

(65) Prior Publication Data
US 2024/0207466 A1  Jun. 27, 2024

Related U.S. Application Data

(60) Provisional application No. 63/062,935, filed on Aug. 7, 2020, provisional application No. 63/014,601, filed on Apr. 23, 2020.

(51) Int. Cl.
  *A61L 2/10*  (2006.01)
  *A61L 2/24*  (2006.01)
  *A61L 2/26*  (2006.01)

(52) U.S. Cl.
  CPC ...... *A61L 2/10* (2013.01); *A61L 2/24* (2013.01); *A61L 2/26* (2013.01); *A61L 2202/11* (2013.01);
  (Continued)

(58) Field of Classification Search
  CPC ...... A61L 2/10; A61L 2/24; A61L 2/26; A61L 2202/11; A61L 2202/14; A61L 2202/25
  See application file for complete search history.

(56) References Cited

U.S. PATENT DOCUMENTS 7,692,172 B2 * 4/2010 Leben .................. B66B 11/024
                                                    250/365
8,742,364 B2   6/2014 Boodaghians et al.
(Continued)

FOREIGN PATENT DOCUMENTS

CN      201068424 Y    6/2008
EP       3293118 A1    3/2018

OTHER PUBLICATIONS

Chinese Application No. 202180030257.X, Office Action mailed on Feb. 26, 2025, 12 pages (8 pages of original document and 4 pages of English Translation).
(Continued)

*Primary Examiner* — Sean M Luck
(74) *Attorney, Agent, or Firm* — Kilpatrick Townsend & Stockton LLP

(57) ABSTRACT

Systems and methods for disinfection of aircraft cabins, including galleys and lavatories. The embodiments may use UVC light sources having a wavelength between 200-230 nm for efficiently inactivating pathogens without harm to exposed mammalian skin or eyes.

20 Claims, 7 Drawing Sheets

(52) U.S. Cl.
CPC ....... *A61L 2202/14* (2013.01); *A61L 2202/25* (2013.01)

(56) References Cited

U.S. PATENT DOCUMENTS

| | | | |
|---|---|---|---|
| 9,061,923 | B2 | 6/2015 | Hsueh et al. |
| 9,260,323 | B2 | 2/2016 | Boodaghians et al. |
| 9,296,480 | B2 | 3/2016 | Boodaghians |
| 9,376,333 | B2 | 6/2016 | Boodaghians et al. |
| 9,540,107 | B2 | 1/2017 | Boodaghians et al. |
| 9,550,006 | B2 | 1/2017 | Boodaghians et al. |
| 9,907,870 | B2 * | 3/2018 | Boodaghians ............ A61L 9/20 |
| 10,266,426 | B1 | 4/2019 | Conrad et al. |
| 10,478,515 | B2 * | 11/2019 | Shur ......................... A61L 2/10 |
| 10,583,213 | B2 * | 3/2020 | Stibich .................... A61L 9/015 |
| 2007/0053188 | A1 | 3/2007 | New et al. |
| 2016/0220716 | A1 | 8/2016 | Childress et al. |
| 2017/0173195 | A1 | 6/2017 | Stibich et al. |
| 2017/0290935 | A1 | 10/2017 | Boodaghians et al. |
| 2018/0064833 | A1 * | 3/2018 | Childress ............... B64D 11/02 |
| 2018/0193501 | A1 * | 7/2018 | Ufkes ....................... A61L 2/10 |
| 2018/0221521 | A1 * | 8/2018 | Shur ......................... A61L 2/00 |
| 2019/0328920 | A1 * | 10/2019 | Stibich ...................... A61L 2/10 |
| 2020/0085983 | A1 * | 3/2020 | Ramanand ................ A61L 2/28 |

OTHER PUBLICATIONS

International Patent Application No. PCT/IB2021/052667, International Search Report and Written Opinion, dated Jun. 30, 2021.
Authors et. al.: Disclosed Anonymously, "Virus and Bacterial Mitigation in Commercial Aircraft ED—Dari Kuhn", ip.com, ip.com Inc., West Henrietta, NY, Aug. 31, 2020 (Aug. 31, 2020), XP013187733, ISSN: 1533-0001.
Welch et al., "Far-UVC light: A new tool to control the spread of airborne-mediated microbial diseases", Scientific Reports, [Online], vol. 8, No. 1, Feb. 9, 2018 (Feb. 8, 2018), p. 2752, XP055814631, DOI: 10.1038/s41598-018-21058-w, https://WWW.nature.com/articles/s41598-018-21058-w.pdf>.

* cited by examiner

FAR-UVC, NARROW-BAND OF DISINFECTING LIGHT, USED IN AIRCRAFT CABIN

CROSS REFERENCE TO RELATED APPLICATIONS

This application is a claims the benefit of priority to U.S. Provisional Application Ser. No. 63/014,601, titled "FAR-UVC, NARROW-BAND OF DISINFECTING LIGHT, USED IN AIRCRAFT CABIN," filed Apr. 23, 2020 and U.S. Provisional Application Ser. No. 63/062,935, titled "FAR-UVC, NARROW-BAND OF DISINFECTING LIGHT, USED IN AIRCRAFT CABIN," filed Aug. 7, 2020, the entire contents of each of which are hereby incorporated by reference.

FIELD OF THE INVENTION

Embodiments of the present invention relate generally to systems and methods for disinfection of aircraft galleys and lavatories and other surfaces. The embodiments may use UVC light sources and/or a disinfection unit powered by a fuel cell or other external power source.

BACKGROUND

Airborne-mediated and surface born microbial (bacterial and virus) diseases such as influenza, COVID, and tuberculosis represent major public health challenges. A direct approach to prevent airborne transmission is inactivation of airborne pathogens. Airborne antimicrobial (bacterial and virus) potential of UVC ultraviolet light has long been established; however, its widespread use in public settings is limited because conventional UVC light sources can be both carcinogenic and cataractogenic.

Aircraft and other passenger transportation vehicle facilities can transport infections, viruses, and bacteria across large distance. This transport can happen very rapidly, due to the very nature of travel. Passenger often travel when knowingly sick, and their coughing, breathing, and/or touching surfaces can spread germs to other passengers. Passengers also travel when, often unknowingly or without any particular symptoms, they have been exposed to a virus or other airborne illness that can be spread rapidly.

Currently, conventional disinfection of aircraft consists of only disinfection gases or liquids that are used to destroy airborne pathogens. While air filtration is possible, it does not prevent person to person transfer of bacteria or virus due to touching of common surfaces or air in the vicinity of passengers. Moreover, this technique is very labor intensive and requires manual actions.

Furthermore, current galley and lavatory cleaning is generally conducted by an airline cleaning company on a frequent basis, and typically during aircraft turn-around times. During these cleaning procedures, chemical disinfection is used to clean exposed surfaces, such as countertops, sinks, trolley doors, and floors. The interior of compartments may also be cleaned on a regular basis, such as ovens, chillers, storage containers, and so forth. During flights, the crew typically only clean the galley or lavatory areas when debris or spillovers are visible. Therefore, additional disinfection is not being carried out during the aircraft flight time. In the lavatory, the toilets, countertops, cabinet doors, sinks, and floors are also cleaned by the cleaning company during aircraft turn-around and/or at the end of scheduled flight service.

Aircraft lavatories provide an environment that is often considered unclean due to the presence of microbiological contamination. There may also be an increased risk for transmissible disease because the standard of hygiene can be very poor in aircraft lavatories, which are used by hundreds of users, without always receiving proper, regular disinfection. Since various pathogens can live for weeks on hard surfaces, various viruses or bacterial infection may spread more easily in aircraft lavatories. Additionally, air traveler immune systems are constantly under assault from lack of circadian rhythms, stress, pesticides and chemicals used in aircraft, foreign environments, and so forth, which can escalate their vulnerability to various pathogens. As the pathogenic landscape continues to morph daily, it is desirable that that health risks associated with contaminated lavatories be addressed.

One proposed solution is the use of UV light to disinfect or sanitize areas. However, these current proposed solutions often require passengers to be absent from the areas being disinfected as they can be harmful to passengers and crew. This further requires complex, heavy, and costly safety measures be in place to avoid any activation of the system during presence of passengers or crews. Improved systems and methods for cleaning cabin surfaces and air are described herein.

BRIEF SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments, a disinfection unit for an aircraft may include at least one UVC light having a wavelength between 200 and 230 nm. The UVC light may be configured to pulse such that the UVC light includes a pulse length having a first and a second period. In the first period, the UVC light may emit light and in the second period the UVC light may not emit light. The UVC light may be configured to emit light in the presence of passengers.

In some embodiments, the UVC light may have a wavelength between 207 and 220 nm.

In some embodiments, the UVC light may be positioned within at least one of an aircraft cabin, an aircraft lavatory, an aircraft galley, or an aircraft bridge. The UVC light may be positioned proximate a visible light source.

In some embodiments, the pulse length may be constant such that each of the first period and the second are constant. In some embodiments, the pulse length may vary such that the first period is different than the second period having varying lengths over time.

The disinfection unit may include at least one proximity sensor that is configured to detect the presence of a passenger. When the proximity sensor detects the presence of a passenger, the proximity sensor may direct the UVC light to pulse at a first rate. When the proximity sensor detects that a passenger is not present, the proximity sensor may direct the UVC light to pulse at a second rate.

According to certain embodiments, a method for disinfecting an aircraft in the presence of passengers using UVC light may include providing a disinfection unit having at least one UVC light with a wavelength between 200 and 230 nm. The method may further include positioning the UVC light within the cabin of the aircraft proximate a visible light and pulsing the UVC light. During pulsing, the UVC light may cycle between a first period, in which the UVC light emits light, and a second period, in which the UVC light does not emit light. The UVC light may be configured to pulse continuously.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Described herein are embodiments of the present disclosure providing systems and methods for disinfection of various surfaces, particularly disinfection of aircraft cabins, galleys, lavatories, as well as airport bridges. The disclosure may comprise a UVC light 12 having a wavelength in the range of 200-230 nm for surface and air disinfection. In particular, the disclosure may include a FAR-UVC light (i.e., 207-222 nm). The application of the disinfection via the UVC light 12 may be continuous during the flight, or part of the flight, and may be applied when passengers are present in the area of disinfection, thereby enabling real-time airborne inactivation as soon as pathogens are emitted from a sick passenger. The disclosure may be applied, for example, within in a cabin of the aircraft, including the aircraft doorways, galleys, passenger seating areas, passenger congregation areas, lavatories, inside overhead bins, or any other areas where disinfection is desired. The disclosure may further be applied in an airport bridge during boarding or deplaning.

According to certain embodiments of the disclosure, the disclosure uses a UVC light 12 with a wavelength between 200-230 nm. In particular, the disclosure may include a FAR-UVC light with a 222 nm. For example, the disclosure may include a lamp or LEDs with an output wavelength of 222 nm and a filter adapted to cut off wavelengths above and/or below a certain threshold (e.g., above and below 222 nm).

Figure 1A:
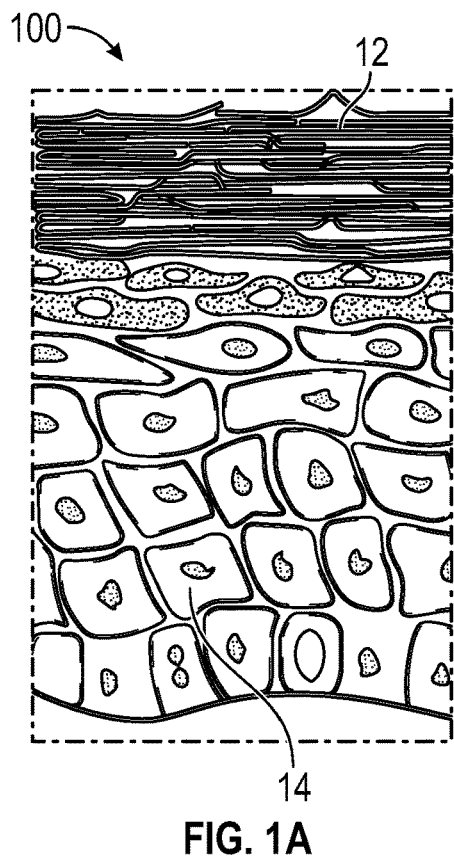
FIGS. 1A-1B shows cross sectional views of penetration of UVC light into layers of skin or eye of a passenger.
Figure 1B:
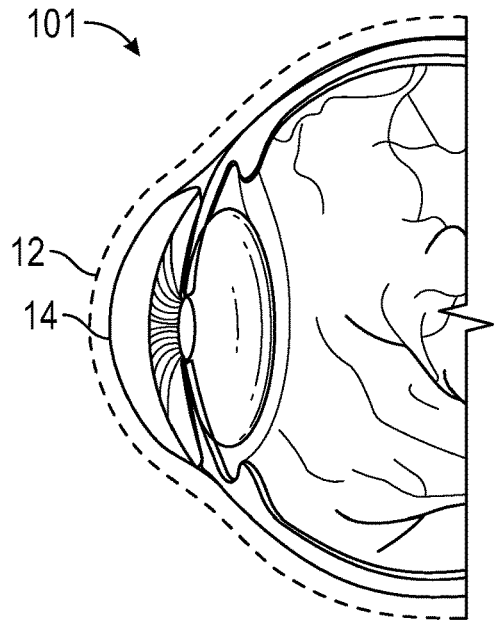
Figure 2:
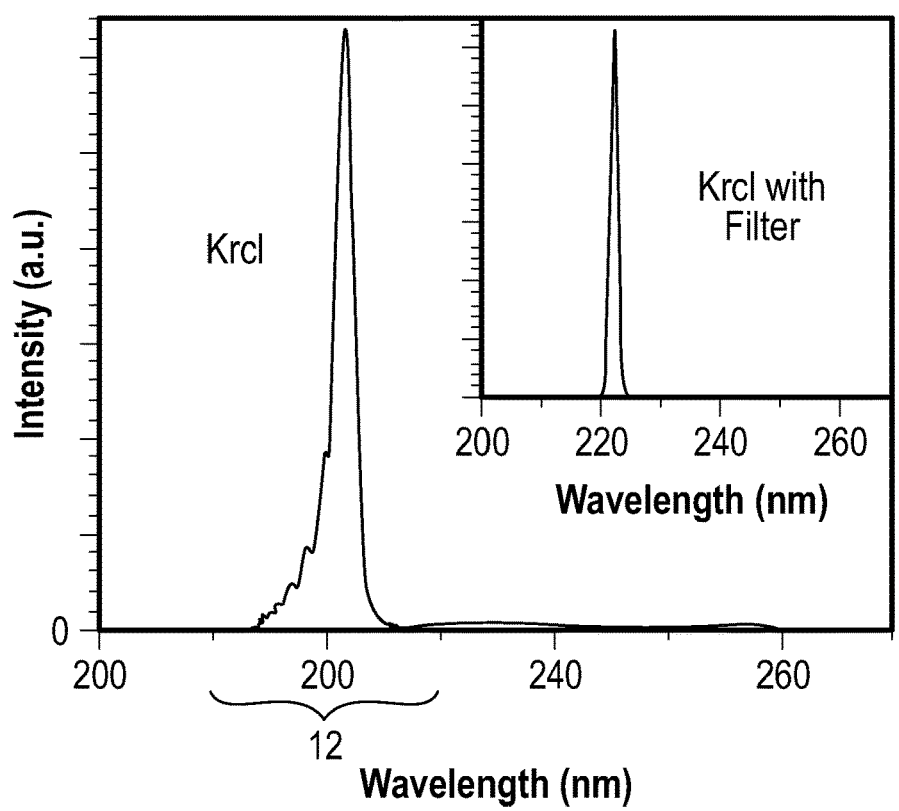
FIG. 2 shows a graph of intensity of UVC light according to wavelength.

As illustrated in FIGS. 1A-1B, at a cellular level, the light emitted from the UVC light 12 may not penetrate deeper than the first micrometers of mammalian skin 100 or eye cells 101. Meanwhile, because bacteria and viruses have micrometer (or smaller) dimensions, the light emitted from the UVC light 12 may penetrate and inactive them. Furthermore, the light emitted from the UVC light 12 may have a strong absorbance in biological materials suitable enough to efficiently inactivate bacteria and viruses, as further illustrated in FIGS. 2A-2B.

As described above, the application of disinfection via the UVC light 12 may be continuous during the flight, or part of the flight, and may be operated while passengers are present thereby allowing for continuous sanitization or disinfection. According to certain embodiments, the disclosure may utilize a pulsing system whereby light emitted by the UVC light 12 is pulsed, thereby limiting exposure of mammalian skin 100 or eyes 101 within regulatory standards. The disclosure may include at least one pulse length. For example, the UVC light 12 may be pulsed such that there is a first period in which the UVC light 12 is emitted for a particular period of time (i.e., defining the pulse length) followed by a second period in which the UVC light 12 is not emitted. The pulse length may vary or may be constant. For example, the pulse length may last for milliseconds, seconds, minutes, or any option thereof. The pulse length may be a function of the distance of the UVC light 12 from the surface to be disinfected. In other words, the closer the UVC light 12 is to the desired surface the less time is required for disinfection.

The efficiency of the disclosure's disinfection, or sanitation, may be linked to the pulsing of the UVC light 12. In other words, the pulsing of the UVC light 12 can be adapted to achieve a certain level of efficiency. For example, the pulse rate (or pulse length) of the UVC light 12 may be adjusted to ensure that a particular surface (e.g., tray table, toilet lid, railing) that may be a certain distance away from the UVC light 12 is disinfected in a certain time. As described above, the disclosure can be pulsed according to varying pulse lengths.

In some embodiments, the disclosure may be preset such that the UVC light 12 is programmed to pulse at preset intervals. In other words, the disclosure may be delivered to the customer in a preprogrammed state. In other embodiments, the crew may be provided with the option to re-program the UVC pulse at differing intervals.

In some embodiments, intensity of the light emitted by the UVC light 12 may be dynamically altered (i.e., raised and/or lowered). In particular, the disclosure may also operate in response to external inputs such as, for example, proximity sensors 34. One example of a proximity sensor is illustrated by FIG. 4C. In this figure, the proximity sensor 34 is mounted to the wall or door of a lavatory. In other examples, the proximity sensor 34 may be mounted to other surfaces of the lavatory, for example, but not limited to, the ceiling, the washstand 26, or any other suitable surface of the lavatory. The proximity sensors 34 may provide dynamic management of the pulsing UVC light 12. The proximity sensor 34 may be used to change the pulse length or duration of UVC light 12 or may be used to dim the dosage of the light emitted by the UVC light 12 (i.e., reduce the power of the UVC light). In some examples, the proximity sensor 34 may operate in a variety of stages. For example, the proximity sensor 34 may detect when a passenger is present and, in response, direct the UVC light 12 to pulse at a first rate (i.e., a first pulse length). The proximity sensor 34 may also detect when a passenger is not present and, in response, can direct the UVC light 12 to pulse at a second rate (i.e., a second pulse length), which may be different from the first rate (i.e., the second pulse length may be longer or shorter than the first pulse length). Additionally, the proximity sensor 34 may detect when a passenger (or object) is too close to the UVC light 12 and, in response, may direct the UVC light 12 to stop pulsing altogether (i.e., the pulse rate is essentially zero) so not to cause unintended harm to a passenger. This dynamic management of the pulsing of the UVC light 12 may be particularly beneficial, for example, when used in an aircraft lavatory. For example, the proximity sensor 34 may be able to indicate when the aircraft lavatory is occupied (e.g., by perceiving when the lavatory light is on or off). When the proximity sensor 34 determines the aircraft lavatory is occupied, it may direct the UVC light 12 to pulse at a first rate (i.e., a pulse length) that is different than the rate at which the UVC light 12 pulses when the lavatory is unoccupied (i.e., the length of the pulse may be longer or shorter depending upon whether the lavatory is occupied). In some examples, the proximity sensor 34 may further detect when a particular area (e.g., the aircraft lavatory) has been disinfected and unoccupied by a passenger for a prolonged period of time. When such a situation is detected, the UVC light 12 may go into a dormant-like state, whereby the UVC light 12 does not continue to pulse at the previous rate (i.e., the previous pulse length), which may aid in prolonging the life of the UVC light 12.

As standards evolve, the pulsing strategy can be optimized, such as, but not limited to, changing the pulse length or duration of the light emitted by the UVC light 12 without the need to change the system other than software. Rather than requiring the UVC light 12 to be completely shut off, as is currently required in conventional systems, the disclosure contemplates changing the pulse length or dimming down the UVC light 12 to control the exposure of the light emitted by the UVC light 12.

By pulsing the UVC light 12, disinfection via the UVC light 12 can potentially make the use of UVC light safer as there is less exposure as compared to the continuous administration of the UVC light 12. Therefore, the disclosure may be used in the presence of passengers and continuously sanitize, or disinfect, areas in a safer manner. For example, the disclosure does not require lavatories, or other areas, to be unoccupied to apply disinfection via the UVC light 12.

In some embodiments, the disclosure includes integrating the UVC light 12 into and/or near a visible light source 18 (e.g., an existing reading light) such that the UVC light 12 is in close proximity to the visible light source 18. For example, as illustrated in FIG. 3D, the UVC light 12 may be positioned along a perimeter of the of the housing of the visible light source 18. As UVC light sources often do not emit much visible light, a passenger may unintentionally look directly into the UVC light source, which is to be avoided even if FAR-UVC will not cause harm to the passenger even and the passenger is exposed within current regulations. Thus, positioning the UVC light 12 in close proximity to the visible light 18 source discourages a passenger from looking into the UVC light 12 as doing so would be uncomfortable, thereby preventing unintentional direct eye sight. The UVC light 12 may be used in conjunction with fixed, mobile, or handheld disinfection UVC lamps.

In some embodiments, the disclosure may be computer controlled such that the disclosure does not require a technician or maintenance crew. However, in other embodiments, the disclosure may be manually operated.

As described above, and illustrated in FIGS. 3-7, the disclosure may be used in in various areas of the cabin, including, but not limited to, the aircraft doorways, galleys, passenger seating areas, passenger congregation areas, lavatories, inside overhead bins, or any other areas where disinfection may be desired.

Figure 3A:
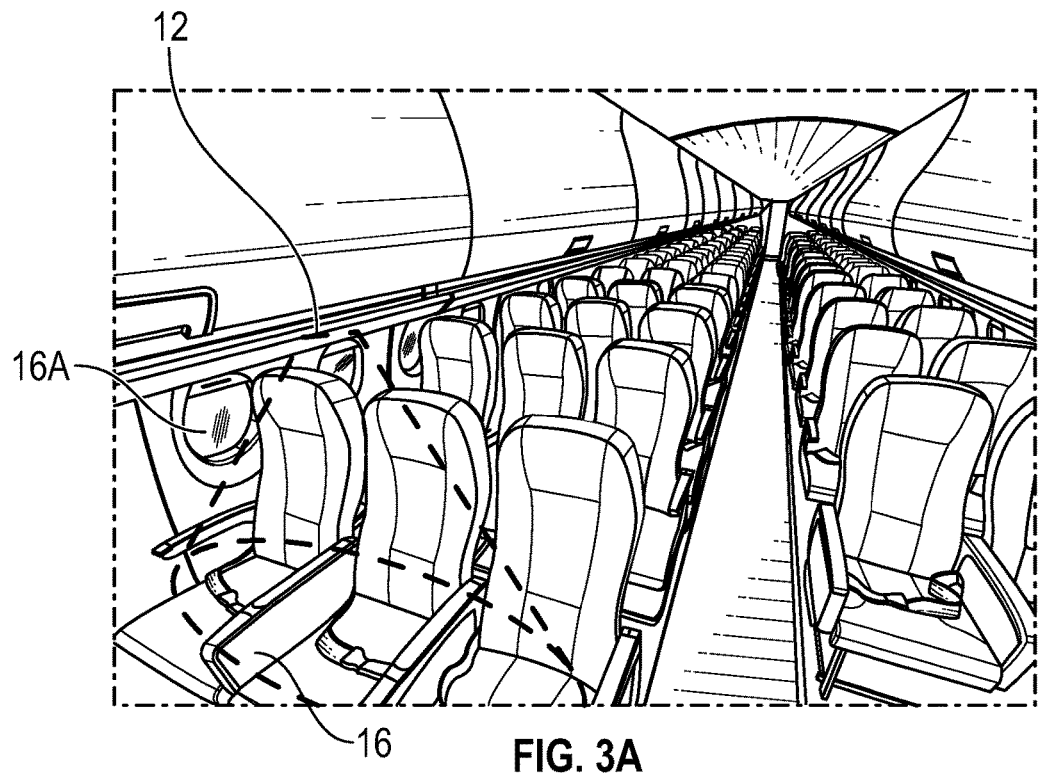
FIGS. 3A-3C show perspective views of one embodiment of the UVC light in the aircraft cabin.
Figure 3B:
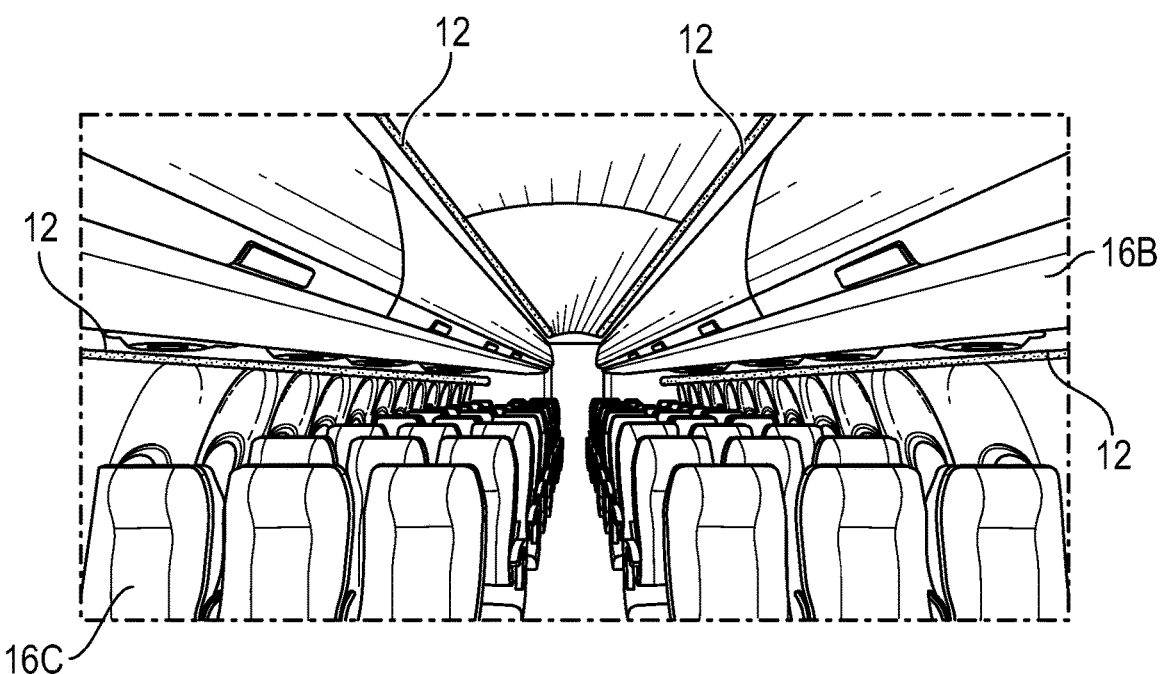
Figure 3C:
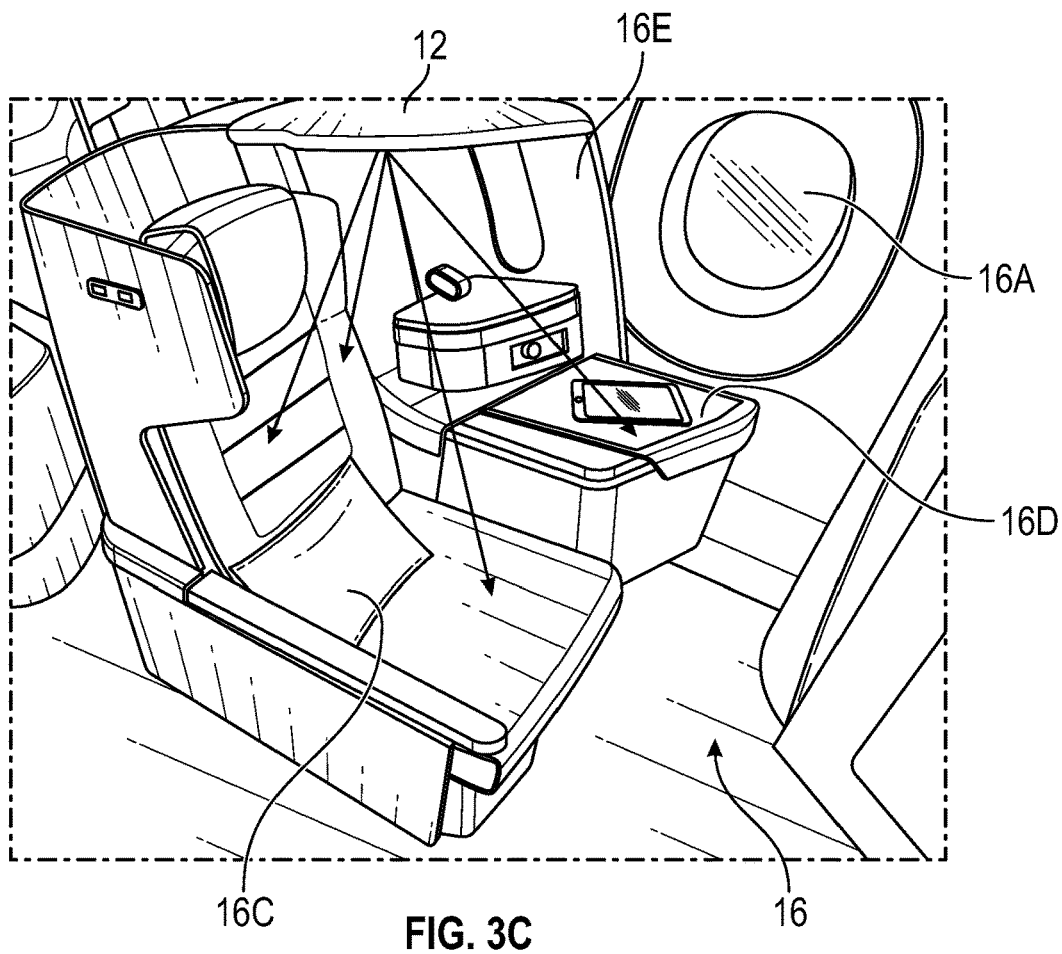
Figure 3D:
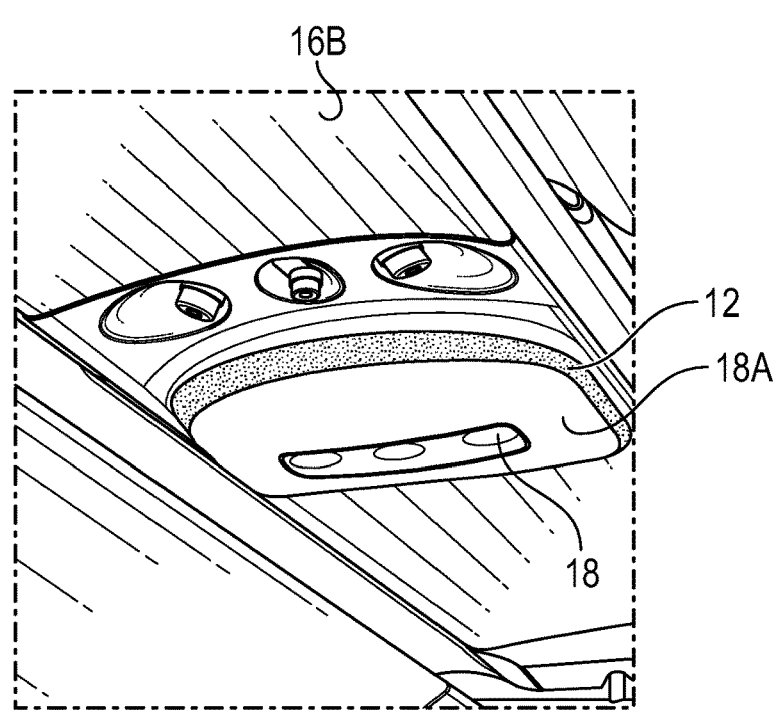
FIG. 3D shows another perspective view of the UVC light integrated into above a seating area of the aircraft cabin.
Figure 3E:
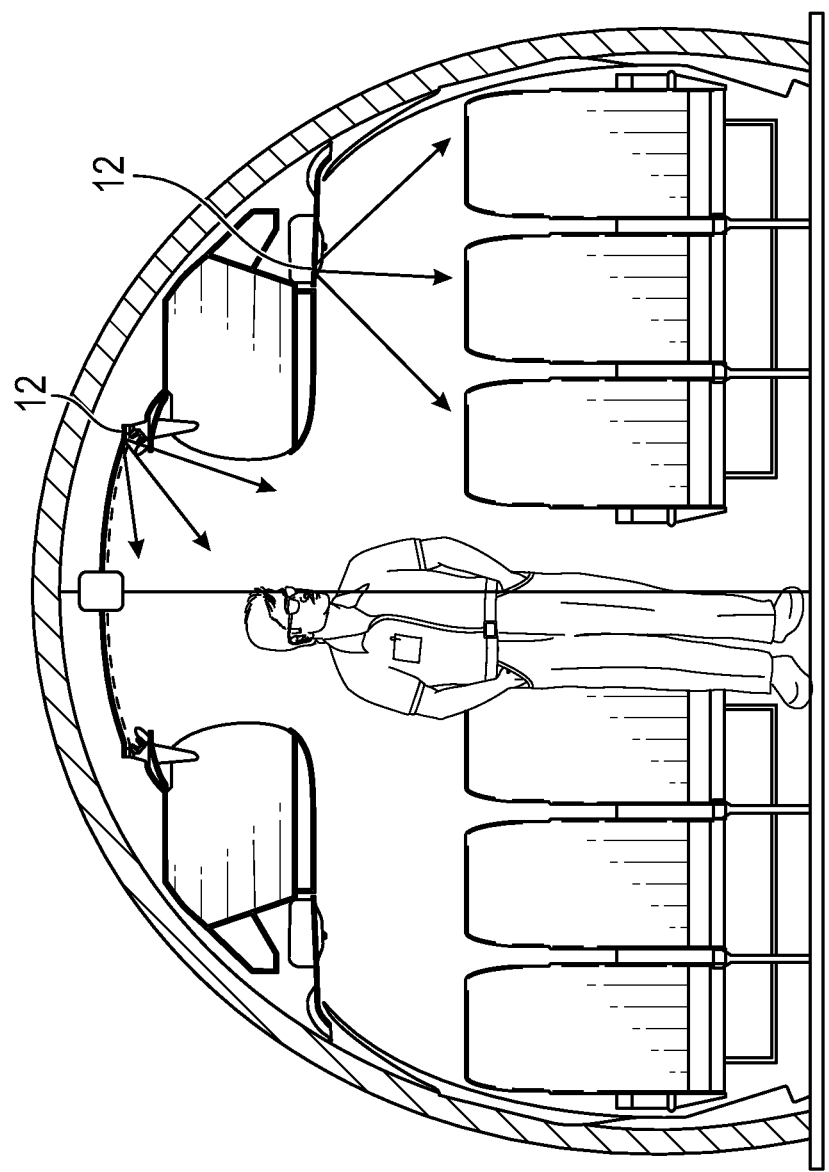
FIG. 3E shows a front view of the flow of the UVC light throughout the aircraft cabin.

In some embodiments, as illustrated in FIGS. 3A-3E, the disclosure may provide surface disinfection, as well as air disinfection areas within the seating areas 16 of the cabin with which passengers have contact. For example, the disclosure may provide disinfection to areas including, but not limited to, seat surfaces, table trays, armrests, IFE screens, seat actuation buttons, passenger lighting or call buttons, or any other suitable surfaces. In some examples, for example as illustrated FIGS. 3A-3B, the UVC light 12 may be disposed along a side of the aircraft cabin proximate cabin windows 16A. The UVC light 12 may also be positioned along a bottom surface of overhead bins 16B, which form the ceiling surface above the passenger seats 16C. For example, as illustrated in FIG. 3D, the UVC light 12 may be disposed proximate In some examples, as illustrated in FIG. 3C, the UVC light 12 may be integrated within a privacy shell 16E of the passenger seat 16C. In particular, the UVC light 12 may be positioned in an overhead region of the privacy shell 16E such that the UVC light 12 can disinfect the passenger seat 16C as well as an adjacent tray table 16D. This configuration may be especially beneficial for use with first class cabin seats. The UVC light 12 may also be integrated into and/or near exiting lights in the aircraft cabin, for example as illustrated in FIG. 3D. As illustrated in FIG. 3D, the UVC light 12 may be disposed proximate a visible light source 18, such as a reading light. In this example, the UVC light 12 may be disposed along a perimeter of a reading light console 18A thereby positioning the UVC light 12 in close proximity to the reading light 18A.

In some examples, the UVC light 12 may be integrated with emergency lighting on the ceiling of the aircraft cabin by integrating the UVC light 12 within the track of the emergency lighting (not shown) such that a number of lightbulbs are replaced with the UVC light 12. For example, the track may replace ever other light, or ever third light, or any suitable interval thereof, with the UVC light 12.

In some examples, the disclosure may include the UVC light 12 as a separate unit, thereby allowing for retrofitting. For example, the UVC light 12 may be a standalone unit that can be moved to different locations. With regard to the placement of the UVC light 12, in some examples, the UVC light 12 may be positioned within reach of a passenger. When the UVC light 12 is positioned within a reachable range of a passenger, the disclosure may include a shield adapted to direct the light emitted by the UVC light 12 ensure the light is not positioned to directly at a passenger. In this way, the light emitted by the UVC light 12 may be focused to illuminate particular surfaces and avoid illumination of unwanted areas. In some examples, the shield may be integrally formed with the UVC light 12. In other examples, the shield may be removably attached to the UVC light 12 and installed during installation of the UVC light 12.

Furthermore, the shield may be removed and reinstalled by a crew member or maintenance as needed.

Figure 4A:
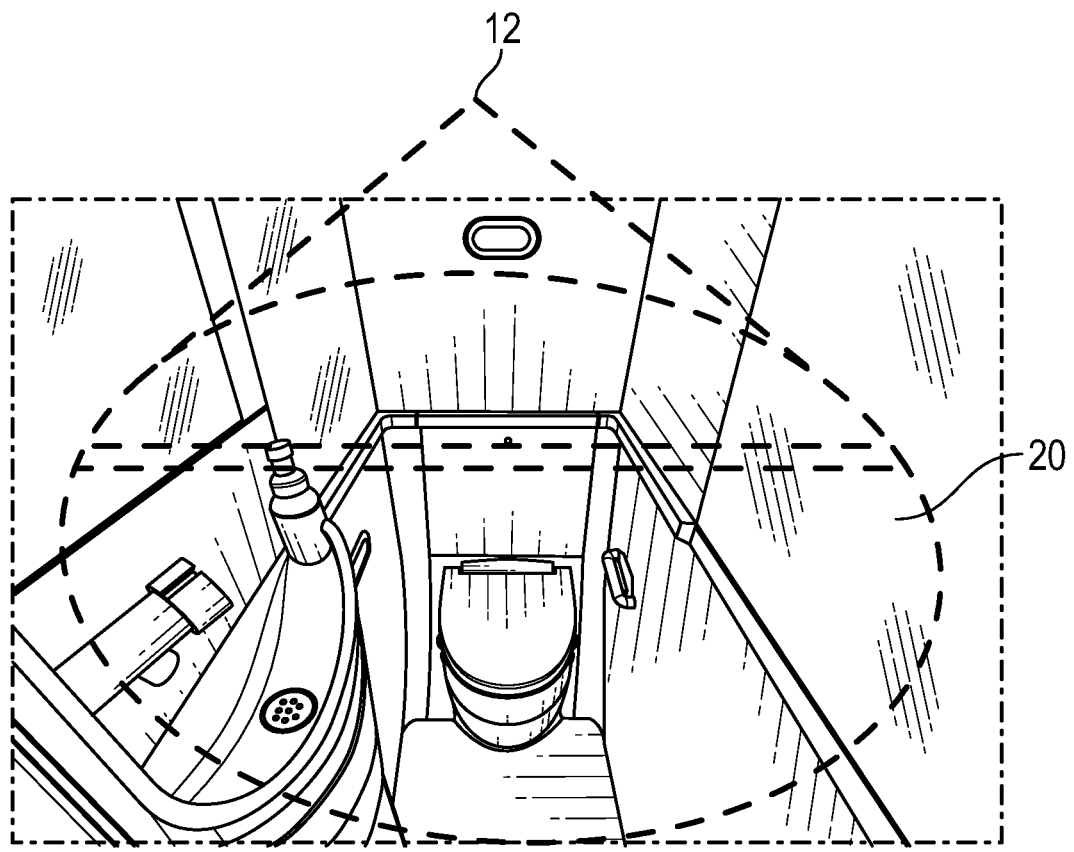
FIGS. 4A-4C show perspective view of the UVC light in an aircraft lavatory.
Figure 4C:
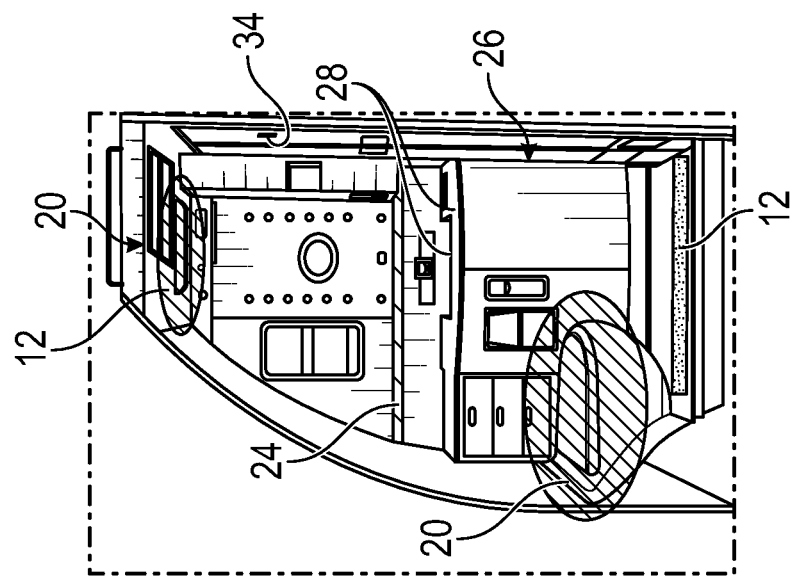
Figure 4B:
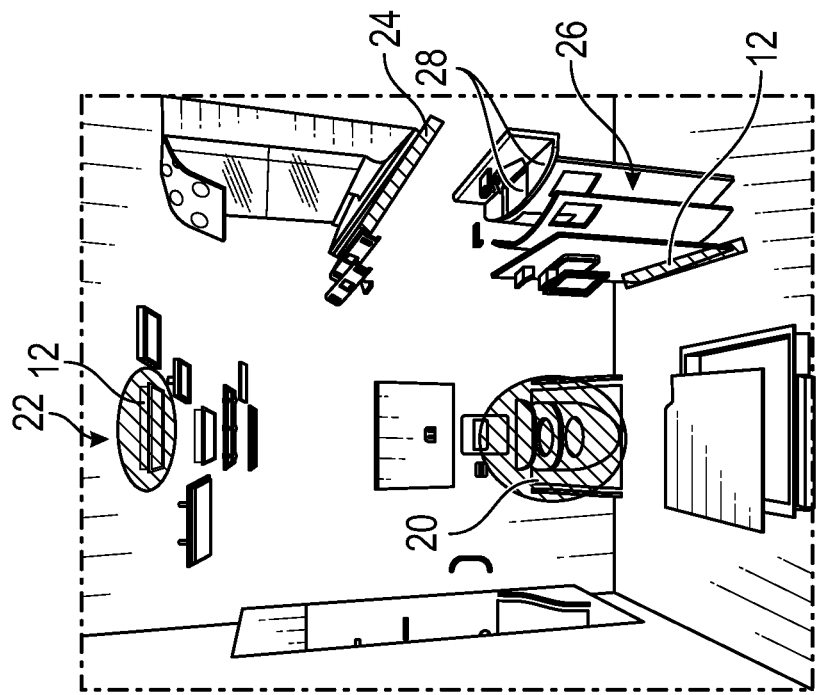

Turning to FIGS. 4A-4C, the UVC light 12 may be integrated into lavatory lighting to provide surface, as well as air, disinfection of the lavatory. The disclosure may be provided for disinfecting lavatory areas including, but not limited to, the toilet bowl, countertop, walls, floor, sink, door, or any other suitable areas within the lavatory. In some embodiments, the UVC light 12 may be integrated into overhead lavatory lighting 22 for disinfecting the toilet seat and/or toilet bowl 20. The UVC light 12 may also be integrated within a light 12 disposed below the mirror 24 for disinfecting the washstand 26, including the sink and the countertop 28. In some embodiments, the disclosure may include a general lamp, which may be installed in the ceiling for disinfecting the entire toilet. This general lamp may be included as a short-term retrofit option.

Figure 5:
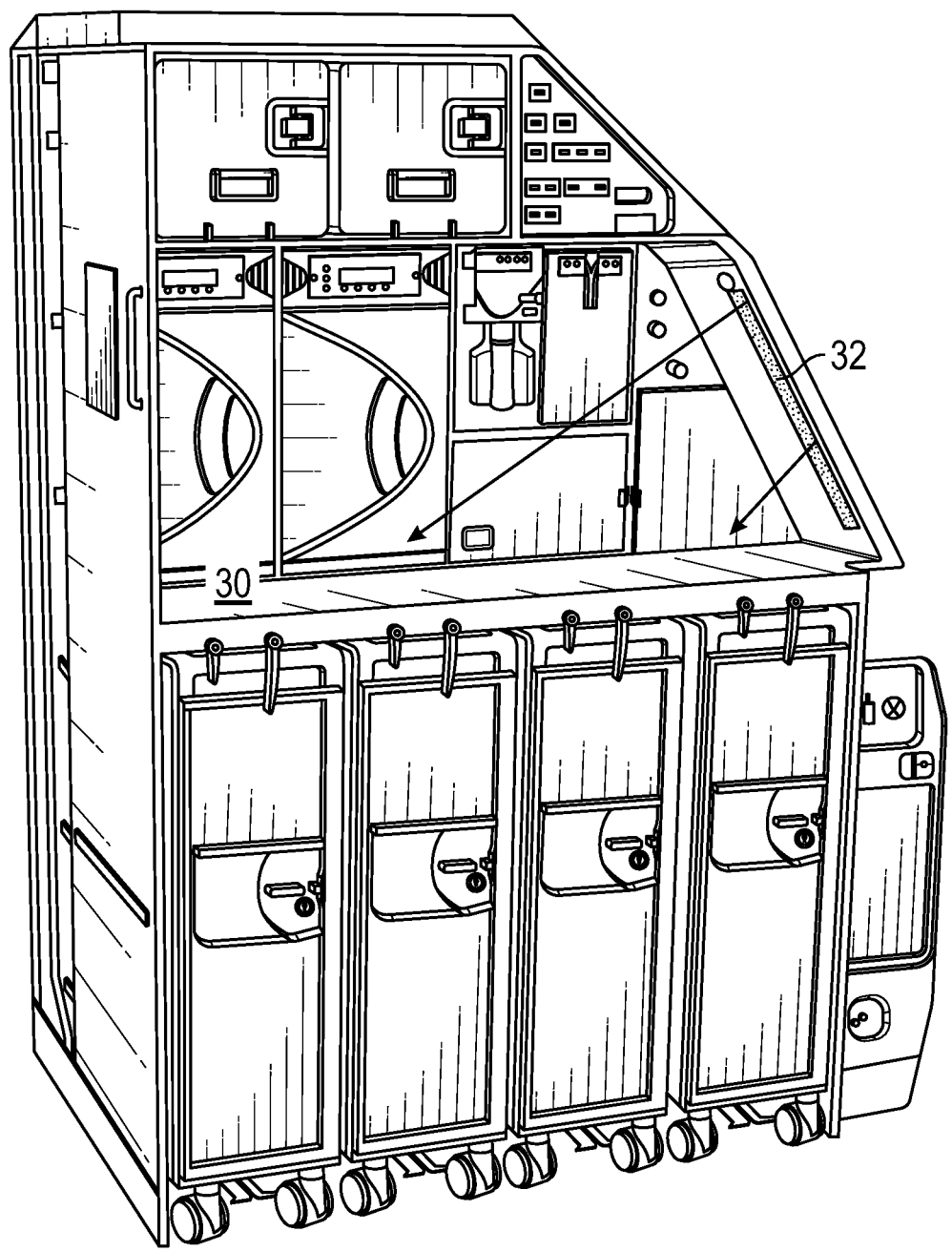
FIG. 5 shows a perspective view of the UVC light in an aircraft galley.

In some embodiments, as illustrated in FIG. 5, the disclosure may be integrated into galley lighting for providing surface, as well as air, disinfection of the galley and entrance area and, thus, avoid contamination of passenger food, beverage, and/or tableware that may be used in self-service (e.g., glasses, utensils, plate ware). The disclosure may further provide for disinfection of areas 30 which may be touched by multiple crew members (e.g., countertop, coffee pots, drawers, cabinets, trolleys). The disclosure may comprise a main disinfection light 32 wherein the UVC light 12 is integrated within the main disinfection light 32 and thereby provide disinfection to the work bench 30 where food may be prepared. Additionally, the UVC light 12 may be positioned in the trolley storage to disinfect the trolleys. Furthermore, the UVC light 12 may be positioned within the ceiling (e.g., integrated within an existing ceiling light) for disinfecting the walls and/or floors of the galley.

In some embodiments, the disclosure may be provided within the airport bridge by integrating the UVC light 12 within airport bridge lighting. The disclosure may provide surface disinfection, as well as air disinfection of the airport bridge, including, but not limited to, walls, railings, or any other suitable areas. Currently, many airports implement social distancing procedures prior to the boarding gate to prevent the spread of airborne pathogens and airborne antimicrobial (bacterial and virus) diseases. However, after passengers pass through the boarding gate and enter the airport bridge, which connects the airport to the aircraft, it can be difficult to implement social distancing procedures. The UVC light 12 may be integrated into the airport bridge, for example within the ceiling in proximity to existing Airport Bridge Lighting. The UVC light 12 may also be integrated as a separate unit, which may be placed in locations within the Airport Bridge.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Example A. A disinfection unit for an aircraft comprising:
at least one UVC light (12) having an wavelength between 200 and 230 nm;

wherein the at least one UVC light (12) is configured to pulse such that the UVC light (12) includes a pulse length having a first period and a second period;

wherein, in the first period, the at least one UVC light (12) emits light;

wherein, in the second period, the at least one UVC light (12) does not emit light;

wherein the at least one UVC light (12) is configured to emit light in the presence of passengers Example B. The disinfection unit of any of the preceding or subsequent examples, wherein the at least one UVC light (12) has a wavelength between 207 and 220 nm.

Example C. The disinfection unit of any of the preceding or subsequent examples, wherein the at least one UVC light (12) is positioned within at least one of an aircraft cabin, an aircraft lavatory, an aircraft galley, or an aircraft bridge.

Example D. The disinfection unit of any of the preceding or subsequent examples, wherein the at least one UVC light (12) is positioned proximate a visible light source.

Example E. The disinfection unit of any of the preceding or subsequent examples, wherein the pulse length is constant such that each of the first period and the second period are constant.

Example F. The disinfection unit of any of the preceding or subsequent examples, wherein the pulse length varies such that the first period is different than the second period and the first period and the second period have varying lengths over time.

Example G. The disinfection unit of any of the preceding or subsequent examples, further comprising at least one proximity sensor (34), wherein the at least one proximity sensor (34) is configured to detect presence of a passenger;

wherein, when the at least one proximity sensor (34) detects the presence of a passenger, the at least one proximity sensor (34) directs the at least one UVC light (12) to pulse at a first rate; and wherein, when the at least one proximity sensor (34) detects a passenger is not present, the at least one proximity sensor directs the at least one UVC light (12) to pulse at a second rate.

Example H. A method for disinfecting an aircraft in a presence of passengers using UVC light (12) comprising:
providing a disinfection unit having at least one UVC light (12) with a wavelength between 200 and 230 nm;

positioning the at least one UVC light (12) within a cabin of the aircraft proximate a visible light (18);

pulsing the at least one UVC light (12), wherein, during pulsing, the at least one UVC light (12) cycles between a first period, wherein the at least one UVC light (12) emits light, and a second period, wherein the at least one UVC light (12) does not emit light; and wherein the at least one UVC light (12) is configured to pulse continuously.

Example I. The method of any of the preceding or subsequent examples, wherein the at least one UVC light (12) has a wavelength between 207 and 220 nm.

Example J. The method of any of the preceding or subsequent examples, wherein the at least one UVC light (12) is positioned within at least one of an aircraft cabin, an aircraft lavatory, an aircraft galley, or an aircraft bridge.

Example K. The method of any of the preceding or subsequent examples, further comprising at least one proximity sensor (34), wherein the at least one proximity sensor (34) is configured to detect presence of a passenger;

wherein, when the at least one proximity sensor (34) detects the presence of a passenger, the at least one proximity sensor directs the at least one UVC light (12) to pulse at a first rate; and wherein, when the at least one proximity sensor (34) detects a passenger is not present, the at least one proximity sensor (34) directs the at least one UVC light (12) to pulse at a second rate.

Example L. A disinfection unit for an aircraft comprising:

at least one UVC light (12) having an wavelength between 200 and 230 nm;

at least one proximity sensor (34) for detecting a presence of a passenger;

wherein the at least one UVC light (12) is configured to pulse such that the UVC light (12) includes a pulse length;

wherein the pulse length comprises a first period, wherein the at least one UVC light (12) emits light, and a second period, wherein the at least one UVC light (12) does not emit light;

wherein, when the at least one proximity sensor (34) detects the presence of a passenger, the at least one proximity sensor directs the at least one UVC light (12) to pulse at a first pulse length; and wherein the at least UVC light (12) is configured to emit light in the presence of passengers.

Example M. The disinfection unit of any of the preceding or subsequent examples, wherein the at least one UVC light (12) has a wavelength between 207 and 220 nm.

Example N. The disinfection unit of any of the preceding or subsequent examples, wherein the at least one UVC light (12) is positioned within at least one of an aircraft cabin, an aircraft lavatory, or an aircraft galley.

Example O. The disinfection unit of any of the preceding or subsequent examples, wherein the at least one UVC light (12) is positioned proximate a visible light source (18).

Example P. The disinfection unit of any of the preceding or subsequent examples, wherein, when the at least one proximity sensor (34) detects a passenger is not present, the at least one proximity sensor directs the at least one UVC light (12) to pulse at a second rate.

Example Q. The disinfection unit of any of the preceding or subsequent examples, wherein the at least one UVC light (12) comprises a dormant state wherein the at least one UVC light (12) does not continue to pulse at a previous pulse rate;

wherein the at least one UVC light (12) enters the dormant state when the at least one proximity sensor (34) does not detect a presence of a passenger for a prolonged period of time.

Example R. The disinfection unit of any of the preceding or subsequent examples, wherein the pulse length is constant such that each of the first period and the second period are constant.

Example S. The disinfection unit of any of the preceding or subsequent examples, wherein the pulse length varies such that the first period is different than the second period and the first period and the second period have varying lengths over time.

Example T. The disinfection unit of any of the preceding or subsequent examples, wherein the at least one UVC light (12) is controlled via a computer.

What is claimed is:

1. A disinfection unit for an aircraft comprising:
   at least one UVC light having an wavelength between 200 and 230 nm;
   wherein the at least one UVC light is configured to pulse such that the UVC light includes a pulse length having a first period and a second period;
   wherein, in the first period, the at least one UVC light emits light;
   wherein, in the second period, the at least one UVC light does not emit light;
   wherein the at least one UVC light is configured to pulse and cycle between the first period and the second period in the presence of passengers.

2. The disinfection unit of claim 1, wherein the at least one UVC light has a wavelength between 207 and 220 nm.

3. The disinfection unit of claim 1, wherein the at least one UVC light is positioned within at least one of an aircraft cabin, an aircraft lavatory, an aircraft galley, or an aircraft bridge.

4. The disinfection unit of claim 3, wherein the at least one UVC light is positioned proximate a visible light source.

5. The disinfection unit of claim 1, wherein the pulse length is constant such that each of the first period and the second period are constant.

6. The disinfection unit of claim 1, wherein the pulse length varies such that the first period is different than the second period and the first period and the second period have varying lengths over time.

7. The disinfection unit of claim 1, further comprising at least one proximity sensor, wherein the at least one proximity sensor is configured to detect presence of a passenger;
   wherein, when the at least one proximity sensor detects the presence of a passenger, the at least one proximity sensor-directs the at least one UVC light to pulse at a first rate; and
   wherein, when the at least one proximity sensor detects a passenger is not present, the at least one proximity sensor directs the at least one UVC light to pulse at a second rate.

8. A method for disinfecting an aircraft in a presence of passengers using UVC light comprising:
   providing a disinfection unit having at least one UVC light with a wavelength between 200 and 230 nm;
   positioning the at least one UVC light within a cabin of the aircraft proximate a visible light;
   pulsing the at least one UVC light, wherein, during pulsing, the at least one UVC light cycles between a first period, wherein the at least one UVC light emits light, and a second period, wherein the at least one UVC light does not emit light; and
   wherein the at least one UVC light is configured to pulse continuously.

9. The method of claim 8, wherein the at least one UVC light has a wavelength between 207 and 220 nm.

10. The method of claim 8, wherein the at least one UVC light is positioned within at least one of an aircraft cabin, an aircraft lavatory, an aircraft galley, or an aircraft bridge.

11. The method of claim 8, further comprising at least one proximity sensor, wherein the at least one proximity sensor is configured to detect presence of a passenger;

wherein, when the at least one proximity sensor detects the presence of a passenger, the at least one proximity sensor directs the at least one UVC light to pulse at a first rate; and wherein, when the at least one proximity sensor detects a passenger is not present, the at least one proximity sensor directs the at least one UVC light to pulse at a second rate.

12. A disinfection unit for an aircraft comprising:
at least one UVC light having an wavelength between 200 and 230 nm;
at least one proximity sensor for detecting a presence of a passenger;
wherein the at least one UVC light is configured to pulse such that the UVC light includes a pulse length;
wherein the pulse length comprises a first period, wherein the at least one UVC light emits light, and a second period, wherein the at least one UVC light does not emit light;
wherein, when the at least one proximity sensor detects the presence of a passenger, the at least one proximity sensor directs the at least one UVC light to pulse at a first pulse length; and
wherein the at least UVC light is configured to emit light in the presence of passengers.

13. The disinfection unit of claim 12, wherein the at least one UVC light has a wavelength between 207 and 220 nm.

14. The disinfection unit of claim 12, wherein the at least one UVC light is positioned within at least one of an aircraft cabin, an aircraft lavatory, or an aircraft galley.

15. The disinfection unit of claim 14, wherein the at least one UVC light is positioned proximate a visible light source.

16. The disinfection unit of claim 12, wherein, when the at least one proximity sensor detects a passenger is not present, the at least one proximity sensor directs the at least one UVC light to pulse at a second rate.

17. The disinfection unit of claim 12, wherein the at least one UVC light comprises a dormant state wherein the at least one UVC light does not continue to pulse at a previous pulse rate;
wherein the at least one UVC light enters the dormant state when the at least one proximity sensor does not detect a presence of a passenger for a prolonged period of time.

18. The disinfection unit of claim 12, wherein the pulse length is constant such that each of the first period and the second period are constant.

19. The disinfection unit of claim 12, wherein the pulse length varies such that the first period is different than the second period and the first period and the second period have varying lengths over time.

20. The disinfection unit of claim 12, wherein the at least one UVC light is controlled via a computer.

* * * * *